(12) United States Patent
Fleury Rey et al.

(10) Patent No.: US 11,484,036 B2
(45) Date of Patent: Nov. 1, 2022

(54) FLAVOUR GENERATION IN FOOD

(71) Applicant: NESTEC S.A., Vevey (CH)

(72) Inventors: Yvette Fleury Rey, Ursy (CH); Christina Vafeiadi, Lausanne (CH); Stephane Duboux, St-Prex (CH); Catherine Ngom-Bru, Montpreveyres (CH); Cassandra Mokdad, Epalinges (CH); Clementine Tastet, Palezieux (CH); Christof Gysler, Blonay (CH); Carl Erik Hansen, Epalinges (CH)

(73) Assignee: Societe des Produits Nestle S.A., Vevey (CH)

( * ) Notice: Subject to any disclaimer, the term of this patent is extended or adjusted under 35 U.S.C. 154(b) by 139 days.

(21) Appl. No.: 16/301,653

(22) PCT Filed: May 16, 2017

(86) PCT No.: PCT/EP2017/061698
§ 371 (c)(1),
(2) Date: Nov. 14, 2018

(87) PCT Pub. No.: WO2017/198650
PCT Pub. Date: Nov. 23, 2017

(65) Prior Publication Data
US 2019/0289861 A1   Sep. 26, 2019

(30) Foreign Application Priority Data
May 19, 2016 (EP) .................................... 16170478

(51) Int. Cl.
*A21D 8/04* (2006.01)
*A23L 27/21* (2016.01)
(Continued)

(52) U.S. Cl.
CPC ............. *A21D 8/042* (2013.01); *A21D 13/36* (2017.01); *A23L 5/25* (2016.08); *A23L 27/215* (2016.08);
(Continued)

(58) Field of Classification Search
CPC . C12N 9/485; C12N 9/48; C12N 9/60; A21D 13/36; A21D 8/042; A23L 5/25;
(Continued)

(56) References Cited

U.S. PATENT DOCUMENTS

| 2003/0186420 A1* | 10/2003 | Ito ........................... C12N 9/48 435/226 |
| 2004/0156980 A1* | 8/2004 | Fleury Rey .............. A21D 2/00 426/656 |
| 2010/0233330 A1* | 9/2010 | Fleury Rey ............ A21D 10/00 426/268 |

FOREIGN PATENT DOCUMENTS

| JP | 07115969 | 5/1995 |
| WO | 9426882 | 11/1994 |
| WO | WO-2005117595 A1 * | 12/2005 ............. A21D 8/042 |

OTHER PUBLICATIONS

JPH07115969—machine translation of description (Year: 1995).*
(Continued)

*Primary Examiner* — Subbalakshmi Prakash
(74) *Attorney, Agent, or Firm* — K&L Gates LLP

(57) ABSTRACT

The present invention relates to flavour generation. In particular the invention relates to a method for flavour generation in a heat-treated food product using a prolidase enzyme. The invention also relates to a heat-treated food product prepared according to the method of the invention.

6 Claims, 7 Drawing Sheets
Specification includes a Sequence Listing.

(51) Int. Cl.
*A21D 13/36* (2017.01)
*C12N 9/48* (2006.01)
*C12N 9/60* (2006.01)
*A23L 5/20* (2016.01)

(52) U.S. Cl.
CPC ............... *C12N 9/48* (2013.01); *C12N 9/485* (2013.01); *C12N 9/60* (2013.01); *C12Y 304/13009* (2013.01); *C12Y 304/21026* (2013.01); *A23V 2002/00* (2013.01); *C12Y 304/11005* (2013.01)

(58) Field of Classification Search
CPC .......... A23L 27/215; C12Y 304/21026; C12Y 304/13009; C12Y 304/11005; A23V 2002/00
USPC .......................................................... 426/18
See application file for complete search history.

(56) References Cited

OTHER PUBLICATIONS

Unknown "SubName: Full=KLLA0A01001p{ECO:00000313|EMBL:CAH02631.1};" Retrieved from EBI accession No. UNIPROT:Q6CYE6, Aug. 16, 2004, 2 pages, XP002761226.

Hoffman, "Influence of L-cysteine on the Formation of Bitter-tasting Aminohexose Reductones From Glucose and L-proline: Identification of a Novel Furo[2,3-b]thiazine", J. Agric. Food Chem, vol. 47, Issue No. 11, 1999, pp. 4763-4768.

European Office Action for Appl No. 17 723 408.5 dated May 26, 2020.

* cited by examiner

SEQUENCE LISTING

<160> NUMBER OF SEQ ID NOS: 1

<210> SEQ ID NO 1
<211> LENGTH: 533
<212> TYPE: PRT
<213> ORGANISM: Kluyveromyces lactis

<400> SEQUENCE: 1

Met Leu Ala Arg Val Phe Pro Lys Arg Ser Ser Phe Ala Ala Asn His
1               5                   10                  15

Thr Ile Lys Thr Thr Val Thr Val Lys Thr Arg Arg Ser Ser Arg Phe
            20                  25                  30

Tyr Ser Lys Leu Ser Ile Asp Asn Asn Asn Leu Arg Lys Ile Lys Met
            35                  40                  45

Ser Ser Ser Val Ala Glu Lys Asn Phe Glu Ser Leu Phe Gln Lys Ile
        50                  55                  60

Asp Glu Leu Lys Pro Arg Phe Ile Glu Arg Leu Ala Lys Ala Ile Glu
65                  70                  75                  80

Ile Pro Ala Val Ser Gly Asp Glu Thr Leu Arg Pro Gln Val Ile Lys
                85                  90                  95

Lys Ala His Tyr Leu Ala Gly Glu Leu Lys Lys Leu Gly Phe Ser Asp
            100                 105                 110

Ile Gln Met Lys Glu Leu Gly Thr Gln Pro Pro Val Ala Asp Pro
            115                 120                 125

Asn Leu Gln Leu Pro Pro Val Ile Leu Ala Arg Tyr Gly Asn Asp Pro
        130                 135                 140

Asp Lys Lys Thr Val Leu Val Tyr Gly His Tyr Asp Val Gln Pro Ala
145                 150                 155                 160

Ser Leu Glu Asp Gly Trp Asn Thr Asp Pro Phe Lys Leu Val Val Asn
                165                 170                 175

Glu Glu Lys Gln Ile Met Tyr Gly Arg Gly Val Ser Asp Asp Ser Gly
            180                 185                 190

Pro Val Lys Gly Trp Leu Asn Val Val Glu Ala His Arg Glu Leu Gly
            195                 200                 205

Leu Asp Leu Pro Val Asn Leu Ile Thr Cys Leu Glu Gly Met Glu Glu
        210                 215                 220

Ser Gly Ser Ile Gly Leu Asp Lys Leu Ile Ala Glu Glu Ala Glu Gly
225                 230                 235                 240

Tyr Phe Arg Thr Val Asp Thr Val Cys Ile Ser Asp Asn Tyr Trp Leu
                245                 250                 255

Gly Thr Gln Lys Pro Val Leu Thr Tyr Gly Leu Arg Gly Cys Asn Tyr
            260                 265                 270

Tyr Gln Ile Ile Ile Glu Gly Pro Gly Ala Asp Leu His Ser Gly Ile
            275                 280                 285

-continued

```
Phe Gly Gly Ser Ile Ser Glu Pro Met Ile Asp Leu Val Gln Val Met
    290             295                 300

Ser Thr Leu Val Asp Thr Lys Gly Asn Ile Leu Ile Asp Gly Ile Lys
305             310                 315                 320

Glu Met Val Ala Pro Val Leu Glu Thr Glu Asp Ala Leu Tyr Asp Lys
                325                 330                 335

Ile Asp Tyr Ser Val Asp Glu Phe Asn Ala Ala Ser Gly Ser Lys Thr
            340                 345                 350

Ala Leu Tyr Asp Asn Lys Lys Asp Ile Leu Met His Arg Trp Arg Tyr
            355                 360                 365

Pro Ser Leu Ser Ile His Gly Val Glu Gly Ala Phe His Gly Ser Gly
    370                 375                 380

Ala Lys Thr Val Ile Pro Ser Lys Val Ile Gly Lys Phe Ser Ile Arg
385                 390                 395                 400

Thr Val Pro Asn Ile Glu Ser Ala Lys Leu Asp Gln Phe Val Ile Asp
                405                 410                 415

His Cys Asn Lys Ala Phe Ala Lys Leu Gln Ser Pro Asn Lys Phe Lys
            420                 425                 430

Ala Glu Leu Ile His Asp Gly Asn Tyr Trp Val Ser Asp Pro Phe Asn
            435                 440                 445

Ala Ser Phe Ser Ala Ala Ala Lys Ala Thr Lys Val Val Trp Gly Val
    450                 455                 460

Glu Pro Asp Phe Thr Arg Glu Gly Gly Ser Ile Pro Ile Thr Leu Thr
465                 470                 475                 480

Phe Glu Gln Glu Leu Lys Ser Asn Val Leu Leu Leu Pro Met Gly Arg
                485                 490                 495

Gly Asp Asp Gly Ala His Ser Ile Asn Glu Lys Leu Asp Leu Ser Asn
                500                 505                 510

Tyr Phe Gly Gly Met Lys Thr Met Ala Ala Tyr Leu His Tyr Tyr Ala
        515                 520                 525

Ala Ser Glu Glu Lys
        530
```

FLAVOUR GENERATION IN FOOD

CROSS REFERENCE TO RELATED APPLICATIONS

The present application is a National Stage of International Application No. PCT/EP2017/061698, filed on May 16, 2017, which claims priority to European Patent Application No. 16170478.8, filed on May 19, 2016, the entire contents of which are being incorporated herein by reference.

FIELD OF THE INVENTION

The present invention relates to flavour generation. In particular the invention relates to a method for flavour generation in a heat-treated food product using a prolidase enzyme. The invention also relates to a heat-treated food product prepared according to the method of the invention.

BACKGROUND OF THE INVENTION

In food, the Maillard reaction results in both the production of flavours and browning (see Bailey, M. E. (1994) Maillard reactions and meat flavour development, pages 153-173, In: Flavour of meat and meat products, Ed. F. Shahidi, Academic Press; Ames, J. M. (1992) The Maillard Reaction, pages 99-143, In: Biochemistry of Food Proteins, Ed. B. J. F. Hudson, Elsevier App. Sci. London).

With respect to flavour generation, the Maillard reaction can be broken down into four stages. The first stage involves the formation of glycosylamines. The second stage involves rearrangement of the glycosylamines to form Amadori and Heyns rearrangement products (often abbreviated in the literature to "ARPs" and "HRPs", respectively). The third stage involves dehydration and or fission of the Amadori and Heyns rearrangement products to furan derivatives, reductones and other carbonyl compounds (which may have significant organoleptic qualities). (These "third stage products" may also be produced without the formation of ARP's or HRP's. The fourth stage involves the conversion of these furan derivatives, reductones and other carbonyl compounds into coloured and aroma/flavour compounds. Thus, products and reactants present in both the third and fourth stage of the Maillard reaction contribute towards aroma/flavour.

Maillard reactions occur naturally in food, but it is also known to use Maillard reaction products to improve the flavour and aroma of foodstuffs.

Amino acids as flavour precursors have been extensively studied in combination with reducing sugars in Maillard reaction systems. Proline was described by Hodge et al. (1972, Cereal Sci Today 17: 3440) as the key amino acid precursor for roast aroma. It was further shown by Schieberle (1990, Z Lebensm Unters Forsch 191: 206-209) that a key impact compound, 2-acetyl-1-pyrroline was generated from proline and ornithine. In U.S. Pat. Nos. 3,687,692 and 3,782,973 it was reported that proline-based reaction mixtures produced a caramel character upon heating with cyclic ketones. U.S. Pat. No. 4,022,920 disclosed that Amadori rearrangement compounds have been produced from proline and 6-deoxy-aldohexoses such as rhamnose under reflux in ethanol followed by drying. The dried mixture was incorporated into a food matrix followed by heating. Among the compounds known to be generated from proline and rhamnose are 4-hydroxy-2,5-dimethyl-3(2H)-furanone and several 2,3-dihydr(IH)-pyrrolizines (Shaw and Ho 1989, Thermal generation of aromas, eds. Parliament T H, McGorrin R J, Ho C-T, American Chemical Society, Washington, D.C.; Shaw et al. 1990, Perfumer & Flavorist 15: 60-66; Tressl et al. 1985, J Agric Food Chem 33: 919-923 and J Agric Food Chem 33: 924-928).

WO2005/117595 describes the use of a proline-specific endoprotease together with an exopeptidase for improving flavour in baked cereal products. For proline-specific endoprotease enzymes that yield a peptide chain with a carboxy-terminal proline residue, WO2005/117595 suggests combining the endoprotease with the carboxypeptidase CPD-Y or a proline-specific carboxypeptidase from *Xanthomonas* or *Escherichia*. However, flavour generation is complex and subtle, with side reactions often playing an important role in the final flavour obtained. The choice of enzymes can influence the character of the flavour generated, as well as the efficiency of generation in different food matrices and conditions, even with enzymes whose primary action is similar.

WO2008/148737 describes a baked food stuff with an improved flavour which is obtained by the addition of flavour precursors (amino acids and reducing sugars) directly to ingredients which are then baked to form baked foodstuffs. Such approach allows formation of the aroma molecules even when the baking duration is short.

Regardless of the advantages provided by the inventions described above to generate flavours in baked food stuffs, they still suffer from some disadvantages.

The use of flavour precursors derived from external sources in order to generate aromas upon heating adds ingredients to the food which may not be familiar to a consumer or expected in food of that type. For example the flavour precursors may not be ingredients that the consumer would use if preparing the food themselves. Many consumer highly appreciate the generation of flavours directly from raw materials which may be used as ingredients in the food products rather than from addition of flavour precursors from external sources. Such raw materials should ideally have good consumer acceptance.

Accordingly, it is advantageous to generate such flavour precursors during the process of preparation of baked foodstuff directly from the raw materials which may be of use as ingredients of the recipe.

Where flavour precursors are generated during the processing of common raw materials it would be desirable to increase the selective production of flavour precursors which lead to attractive roast or baked flavours, for example it would be desirable to increase the selective production of free amino acids such as proline. Efficient production of target flavour precursors allows faster flavour generation processes, more intense flavour generation and avoids the generation of undesirable flavours from the generation of non-target precursors. It would also be advantageous to provide alternatives to known enzymes generating flavour precursors, allowing the formation of different flavour notes and the creation of new flavour profiles for products. Where such a flavour profile becomes associated with a branded food product it is sometimes described as a "signature flavour". Even subtle differences in flavour can be important to the success of a product.

Where enzymes are used to perform conversions of raw material, for example during the food preparation process, it is desirable that these enzymes, and the form in which they are added, have good consumer acceptability. It would be preferable to use enzymes derived from microorganisms with good consumer acceptance, for example microorganisms with a long history of use in food. Many consumers do not wish to have genetically modified microorganisms associated with the production of their food so it is advantageous to achieve the generation of flavour precursors without the use of a genetically modified microorganisms.

Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to".

SUMMARY OF THE INVENTION

An object of the present invention is to improve the state of the art and to provide a solution to overcome at least some of the inconveniences described above or at least to provide a useful alternative. The object of the present invention is achieved by the subject matter of the independent claims. The dependent claims further develop the idea of the present invention.

Accordingly, the present invention provides in a first aspect a method for flavour generation comprising; (a) contacting an edible peptide-containing material with a prolidase to form a hydrolysed preparation, wherein the prolidase comprises an amino acid sequence having at least 95% identity to SEQ ID NO:1; (b) incorporating the hydrolysed preparation obtainable from step (a) into a food preparation which comprises at least a reducing sugar; or, where the hydrolysed preparation already comprises at least a reducing sugar, the hydrolysed preparation may be the food preparation; and (c) subjecting the food preparation to heat treatment to obtain a heat-treated food product.

In a second aspect, the invention relates to a hydrolysed preparation obtainable by contacting an edible peptide-containing material with a prolidase, wherein the prolidase comprises an amino acid sequence having at least 95% identity to SEQ ID NO:1.

A third aspect of the invention relates to a food preparation comprising a prolyl endopeptidase, a prolidase, proline as free amino acid and ornithine as a free amino acid; wherein the prolidase comprises an amino acid sequence having at least 95% identity to SEQ ID NO:1; and, if leucine is present as a free amino acid, the molar ratio of proline to leucine as free amino acids is greater than 2.5 and the molar ratio of ornithine to leucine as free amino acids is greater than 1.

Still further aspects of the invention are a heat-treated food product obtainable according to the method of the invention and the use of a prolidase comprising an amino acid sequence having at least 95% identity to SEQ ID NO:1 to improve the flavour of a heat-treated food product.

It has been surprisingly found by the inventors that particularly good baked flavours can be obtained by using a prolidase comprising an amino acid sequence having at least 95% identity to SEQ ID NO:1 to hydrolyse edible peptide-containing material and then combining with a reducing sugar and applying heat. In particular, proline can be selectively liberated from food proteins and food polypeptides in a highly efficient manner by combining a prolyl endopeptidase with a prolidase comprising an amino acid sequence having at least 95% identity to SEQ ID NO:1. When the resulting mixture is further processed by heating it in a food preparation comprising a reducing sugar, attractive flavours are produced, having baked and toasted notes. The use of a prolidase comprising an amino acid sequence having at least 95% identity to SEQ ID NO:1 surprisingly provides a particularly attractive flavour profile. Compared to the combination of a prolyl endopeptidase and the prolidase CPD-Y, a higher specificity towards proline production was surprisingly observed.

The method according to the invention presents the advantage of delivering flavour notes in heat-treated food products without the need to add amino acids as flavour precursors during the process.

DETAILED DESCRIPTION OF THE INVENTION

Figure 1:
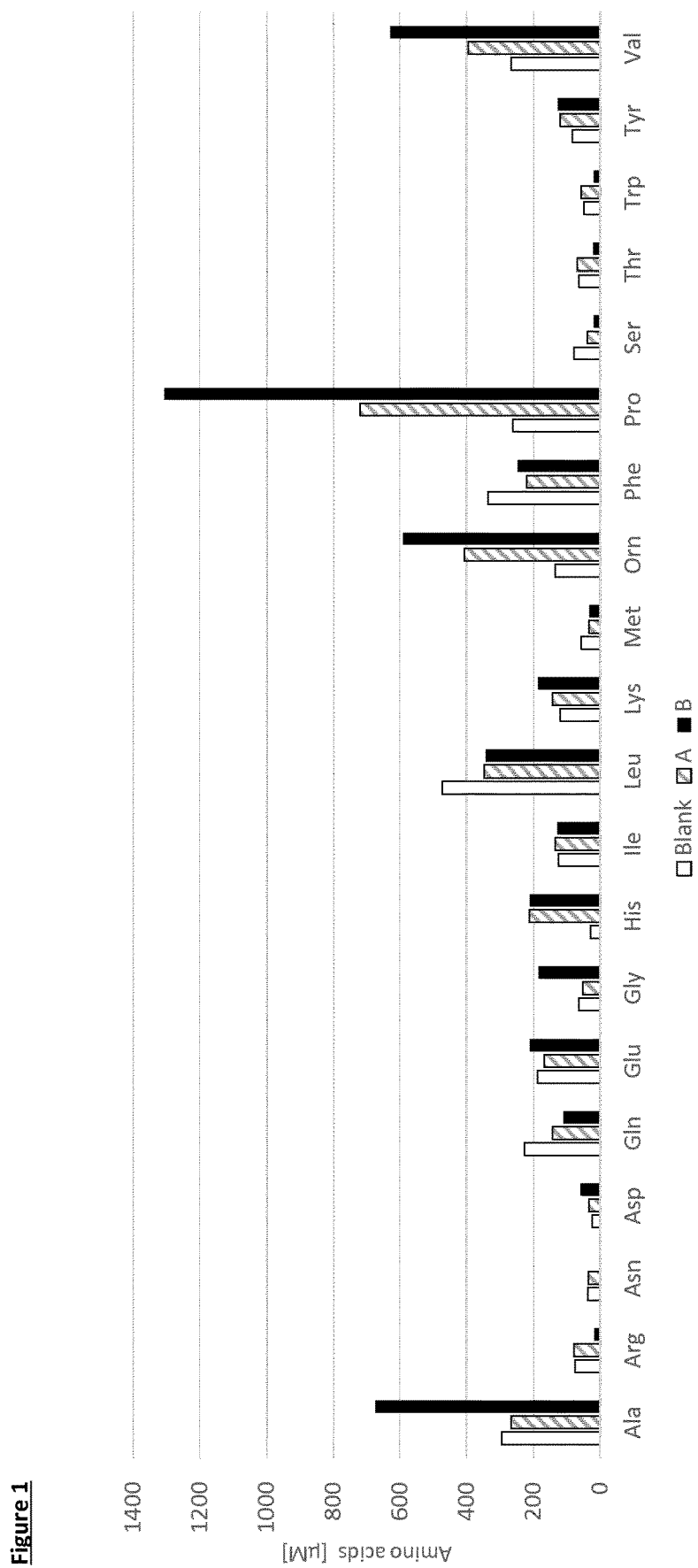
FIG. 1 is a plot of free amino acid quantity (μM) in unreacted wheat gluten (Blank), wheat gluten reacted with prolyl endopeptidase and $K.$ $lactis$ prolidase (B) and wheat gluten with prolyl endopeptidase alone (A). The amino acids are Alanine (ala), Arginine (arg), Asparagine (asn), Aspartic acid (asp), Glutamine (gln), Glutamic acid (glu), Glycine (gly), Histidine (his), Isoleucine (ile), Leucine (leu), Lysine (lys), Methionine (met), Ornithine (orn), Phenylalanine (phe), Proline (pro), Serine (ser), Threonine (thr), Tryptophan (trp), Tyrosine (tyr), Valine (val).

Consequently the present invention relates in part to a method for flavour generation (for example in a heat-treated food product) comprising; a) contacting an edible peptide-containing material with a prolidase to form a hydrolysed preparation, wherein the prolidase comprises an amino acid sequence having at least 95% identity to SEQ ID NO:1; b)

incorporating the hydrolysed preparation obtainable from step (a) into a food preparation which comprises at least a reducing sugar; or, where the hydrolysed preparation already comprises at least a reducing sugar, the hydrolysed preparation may be the food preparation; and c) subjecting the food preparation to heat treatment to obtain a heat-treated food product.

The term flavour is used in the present invention to refer to the combination of taste and aroma. Taste refers to the sensation of flavour perceived in the mouth and aroma refers to perception inside the nose. Chemically, a "flavour" may be one or more taste active molecules, one or more aroma molecules, or a mixture of these. Some taste active molecules are also aroma molecules.

Within the context of the present invention, the term "heat-treated food product" identifies a food product which has been subject to heat treatment. A food product is a substance that can be used or prepared for use as food. Non-limiting examples of heat treating techniques are: oven baking, roller drying, extrusion, spray drying. Non limiting examples of heat treated food products according to the present invention are: biscuits, wafers, cereals (breakfast and infant), bread, ice-cream cones, milk powder, non-dairy beverage creamers, pizza and the like.

The term "edible" is used in the context of the present invention to mean substances which can be eaten safely. Whilst the current invention is not limited to substances permitted for consumption in any particular jurisdiction, edible compositions may for example comprise materials approved for human consumption by the U.S. Food and Drug Administration.

The peptide-containing material according to the invention may be comprise a polypeptide. The peptide-containing material according to the invention may comprise proline. The peptide-containing material may comprise a protein. Proteins consist of one or more polypeptides arranged in a biologically functional way. The peptide-containing material according to the invention may be a protein-containing food ingredient such as wheat flour or milk. Preferably the peptide-containing material comprises polypeptides which have more than 10 amino acids. The peptide-containing material may be a peptone, a water-soluble mixture of polypeptides and amino acids formed by the partial hydrolysis of protein.

A prolidase is an enzyme that catalyzes the hydrolysis of the peptide bond between an amino acid and proline or hydroxyproline. In the context of the current invention the prolidase may be a proline dipeptidase, but it may also catalyse the hydrolysis of the peptide bond of larger peptides such as tripeptides or tetrapeptides that have proline as the terminal amino acid.

The prolidase may comprise an amino acid sequence having at least 97%, 98% or 99% identity to SEQ ID NO:1. For example the prolidase may have the amino acid sequence shown in SEQ ID NO:1.

```
                                        (SEQ ID NO: 1)
MLARVFPKRSSFAANHTIKTTVTVKTRRSSRFYSKLSIDNNNLRKIKMSS

SVAEKNFESLFQKIDELKPRFIERLAKAIEIPAVSGDETLRPQVIKKAHY

LAGELKKLGFSDIQMKELGTQPPPVADPNLQLPPVILARYGNDPDKKTVL

VYGHYDVQPASLEDGWNTDPFKLVVNEEKQIMYGRGVSDDSGPVKGWLNV

VEAHRELGLDLPVNLITCLEGMEESGSIGLDKLIAEEAEGYFRTVDTVCI
```

```
                                         -continued
SDNYWLGTQKPVLTYGLRGCNYYQIIIEGPGADLHSGIFGGSISEPMIDL

VQVMSTLVDTKGNILIDGIKEMVAPVLETEDALYDKIDYSVDEFNAASGS

KTALYDNKKDILMHRWRYPSLSIHGVEGAFHGSGAKTVIPSKVIGKFSIR

TVPNIESAKLDQFVIDHCNKAFAKLQSPNKFKAELIHDGNYWVSDPFNAS

FSAAAKATKVVWGVEPDFTREGGSIPITLTFEQELKSNVLLLPMGRGDDG

AHSINEKLDLSNYFGGMKTMAAYLHYYAASEEK
```

Within the context of the present invention the term "hydrolysed preparation" identifies a composition based on the edible peptide-containing material and comprising any substance generated by the proteolytic action on the edible peptide-containing material of the enzymes present. If the enzymes are generated in-situ, for example by the activities of microorganisms, then the hydrolysed preparation may comprise the microorganisms and/or their residues. Within the context of the present invention, the term "microorganism" identifies a unicellular organism being a bacterium, a filamentous fungi or a yeast. The hydrolysed preparation according to the invention may comprise proline as a free amino acid.

Within the context of the present invention the term "food preparation" identifies a mixture of ingredients which is meant to deliver a "heat treated food product" when subjected to heat treatment. Non limiting examples of "food preparation" are: batters, doughs, mixtures comprising cereals and milk powder, mixtures comprising milk powder and flour, and the like. Within the context of the present invention the terms "dough" or "batter" identify a food ingredient mixture as above defined which is mainly based on cereal flour and water in different ratios. Such dough or batter may also comprise additional ingredients such as for example fats, salts, sugars, eggs, milk and the like.

Within the context of the present invention, the term "reducing sugar" identifies any sugar that either has an aldehyde group or is capable of forming one in solution through isomerisation, such aldehyde group allowing the sugar to act as a reducing agent. The reducing sugar in the current invention may be a mono or oligosaccharide, for example a mono to tetra-saccharide. The reducing sugar may be selected from the group consisting of C5 and C6 monosaccharides. The reducing sugar may be selected from the group consisting of fructose, glucose, xylose, tagatose, rhamnose, maltose, lactose, fucose, arabinose, galactose and mixtures thereof. The reducing sugar may be selected from the group consisting of fructose, glucose or rhamnose. The reducing sugar may be rhamnose.

The prolidase according to the method of the invention may be obtainable (for example obtained) from *Klyveromyces lactis*. Yeasts have good consumer acceptance in food processing due to their long history of use. The prolidase according to the method of the invention may be comprised within a yeast preparation, for example a yeast preparation comprising lysed cells of *Klyveromyces lactis*. The prolidase according to the method of the invention may be obtainable (for example obtained) from *Klyveromyces lactis* CBS 2621 or CBS 141. Both these yeast strains are publically available from CBS-KNAW Collections, The Netherlands. The prolidase may be the prolidase from *Klyveromyces lactis* having the UniProtKB accession number Q6CYE6. This enzyme has the amino acid sequence shown in SEQ ID NO:1.

The prolidase according to the method of the invention may be obtainable (for example obtained) by the autolysis of *Klyveromyces lactis*. The autolysis of *Klyveromyces lactis* cells starts once the growth phase has ended due to nutrient (for example sugar) depletion. This autolysis releases enzymes. In the case of food products it may be beneficial to introduce a yeast into the food production process rather than a pure enzyme. Including yeast which undergoes autolysis presents the operational advantage that, in the hydrolysed preparation, prolidase is delivered spontaneously and amino acid flavour precursors are generated without any need for external intervention on the medium. Such hydrolysed preparation can be thus simply incorporated into the food preparation (batter or dough for example) for its standard further processing. Furthermore, as the structure of the heat-treated food product forms at the same time as the flavour active molecules are generated, the flavour active molecules become trapped within the food matrix and the desirable notes are strong in the finished foodstuff.

Within the context of the present invention, the term "autolysis" identifies a spontaneous process whereby a microorganism cell disrupts and the intracellular content of a microorganism is released in the growth medium.

The prolidase according to the method of the invention may be obtained by growing *Klyveromyces lactis* cells under suitable conditions in a protein containing medium, and allowing the *Klyveromyces lactis* cells to autolyse due to nutrient depletion from the medium. Where all the components of the protein containing medium are food grade, the medium and the lysed *Klyveromyces lactis* cells may be incorporated into the hydrolysed preparation of the method of the invention. Indeed, the liberation of prolidase by autolysis of *Klyveromyces lactis* may be directly part of the food product production process, so-called "in-process" generation of enzymes.

Within the context of the present invention, the term "suitable conditions" for the growth of a microorganism identifies temperature and atmosphere conditions which are appropriate to allow growth of specific microorganisms. Within the context of the present invention the term "protein containing medium" identifies a growth medium for microorganisms which comprises, micronutrients, nitrogen sources and carbon sources. If not already provided by the above mentioned nitrogen sources, the medium also incorporates sources of amino acids such as proteins, peptides or protein hydrolysates.

A method for flavour generation may comprise; a) growing under suitable conditions and in a protein containing medium a microorganism (for example *Klyveromyces lactis*) which autolyses within 7 days after nutrients depletion from the medium; b) maintaining the micro-organism containing growth medium obtainable from step a) under said suitable conditions for period lasting up to 10 days after nutrients depletion; c) incorporating the fermented preparation obtainable form step b) into a food preparation which comprises at least a reducing sugar; d) subjecting the food preparation to heat treatment to obtain a heat-treated food product.

In one embodiment of the method of the invention, the edible peptide-containing material is contacted with a prolyl endopeptidase in addition to a prolidase. For example, the edible peptide-containing material may be contacted with a prolyl endopeptidase before, or simultaneously with being contacted with the prolidase. The prolyl endopeptidase may be a proline-specific endoprotease that yields a peptide chain with a carboxy-terminal proline residue. The prolyl endopeptidase may be a proline-specific endoprotease from *Aspergillus niger*, for example the prolyl endopeptidase may be Maxipro PSP or Maxipro XF from DSM.

In one embodiment, the method of the invention generates a hydrolysed preparation comprising a mixture of several free amino acids. For example, the mixture of several free amino acids generated according to the invention may comprise proline, lysine, alanine, glutamine, valine, arginine, phenyl alanine and ornithine. The mixture of several free amino acids generated in the hydrolysed preparation according to the invention may comprise proline, lysine, glutamine, phenyl alanine and ornithine. The mixture of free amino acids generated according to the invention may comprise proline, lysine, glutamine and phenyl alanine, with proline being the free amino acid with the highest molar fraction in such mixture. In an embodiment, in the mixture of free amino acids generated in the hydrolysed preparation according to the invention, asparagine may be substantially absent. In an embodiment, the mixture of free amino acids generated in the hydrolysed preparation according to the invention may comprise a mixture of free amino acids wherein proline, lysine, glutamine and phenylalanine are present at a concentration greater than 1 mM respectively (for example greater than 2 mM respectively). The mixture of free amino acids generated in the hydrolysed preparation according to the invention may comprise a mixture of free amino acids wherein proline is present at a concentration greater than 5 mM.

The food preparation according to the method of the invention may contain flour. In one embodiment, the amount of individual free amino acids in the food preparation according to the method of the invention ranges between 0.001 and 1 parts in weight based on 100 parts of flour. For example, the amount of free amino acids in a food preparation according to the method of the invention may range between 0.005 and 0.1 parts in weight based on 100 parts of flour. The amount of free amino acids in a food preparation according to the method of the invention may range between 0.05 and 0.1 parts in weight based on flour weight.

In an embodiment, the term "heat-treated food product" identifies a product which is dough- or batter-based. The said batter or dough may comprise:
Flour: 100 parts
Water: from 5 to 200 parts
Salts: from 0.1 to 5 parts
Fat: from 0.1 to 100 parts
Eggs: from 0 to 100 parts
Sugar: from 0 to 100 parts
For example, the said batter or dough may comprise:
Flour: 100 parts
Water: from 100 to 180 parts
Salts: from 0 to 5 parts
Fat: from 0.5 to 2 parts
Sugar: from 0 to 5 parts Particularly when pure enzymes are used, the hydrolysed preparation according to the method of the invention may contain at least a reducing sugar and be the food preparation. For example, a prolyl endopeptidase and a prolidase comprising an amino acid sequence having at least 95% identity to SEQ ID NO:1 may be added directly to a batter composition as above containing a reducing sugar. When enzymes generated in-situ from microorganisms are used it may be preferable to generate the hydrolysed preparation separately from the main ingredients. In an embodiment, the hydrolysed preparation according to the invention may be incorporated into the food preparation in an amount of from 0.05 to 5 parts in dry weight based on 100 parts of flour. For example, the hydrolysed preparation according to the invention may be incorporated into the food preparation in an amount of from 0.1 to 3 parts in dry weight based on 100 parts of flour.

The hydrolysed preparation according to the method of the invention may be incorporated into the food preparation in an amount of 0.01 to 5 parts by weight of the food preparation. Such levels are appropriate for good flavour generation in the presence of reducing sugars.

In one embodiment, the method of the invention provides a heat-treated food product comprising at least one the of the flavour characteristics: biscuit, buttery, fruity, nutty, caramel, golden syrup, honey, toasted, roasted bread-like and baked. For example, the method of the invention may provide a heat-treated food product comprising a biscuit flavour. In one embodiment, the method of the invention provides a heat-treated food product wherein the heat-treated food product comprises cereal flour (for example wheat flour).

The heat treated food product according to the method of the invention may be selected from the group consisting of biscuit, extruded cereal (for example breakfast cereal), pizza (for example pizza base), beverage powder and caramel.

The biscuit may be a wafer. Wafers are baked products which are made from wafer batter and have crisp, brittle and fragile consistency. They are thin, with an overall thickness usually between <1 and 4 mm and typical product densities range from 0.1 to 0.3 g/cm$^3$. The surfaces are precisely formed, following the surface shape of the plates between which they were baked. They often carry a pattern on one surface or on both. Wafers may also be produced by extrusion. Two basic types of wafer are described by K. F. Tiefenbacher in "Encyclopaedia of Food Science, Food Technology and Nutrition p 417-420—Academic Press Ltd London—1993":

1) No- or low-sugar wafers. The finished biscuits contain from zero to a low percentage of sucrose or other sugars. Typical products are flat and hollow wafer sheets, moulded cones or fancy shapes.

2) High-sugar wafers. More than 10% of sucrose or other sugars are responsible for the plasticity of the freshly baked sheets. They can be formed into different shapes before sugar recrystallization occurs. Typical products are moulded and rolled sugar cones, rolled wafer sticks and deep-formed fancy shapes.

The beverage powder may be a heat-treated milk powder, a cocoa or malt beverage powder or a beverage creamer such as a dairy or non-dairy creamer for use with coffee.

Within the context of the present invention, caramel is a confectionery product made by heating a variety of sugars, for example as sugar syrups in water. Milk ingredients such as skimmed milk powder or condensed milk are typically heated together with the sugar syrups. The caramel may be liquid, or it may have undergone a degree of sugar crystallization to form a solid. It is typically brown in colour and is often found as a filling in chocolate confectionery products.

The edible peptide-containing material according to the method of the invention may be selected from the group consisting of flour (for example wheat flour), milk and peptide-containing components of these, for example gluten (a component of wheat flour) or casein (a component of milk). The edible peptide-containing material according to the method of the invention may be a protein hydrolysate such as a casein hydrolysate.

In an embodiment of the method of the invention the edible peptide-containing material, the prolyl endopeptidase and the prolidase may be contacted in an aqueous dispersion at a temperature of between 30 and 60° C., for example between 45 and 55° C. The edible peptide-containing material, the prolyl endopeptidase and the prolidase may be contacted in an aqueous dispersion at a pH between 5.0 and 8.5.

In an embodiment of the method of the invention the edible peptide-containing material may be contacted with the prolyl endopeptidase and the prolidase sequentially or simultaneously. In the embodiment where the edible peptide-containing material is contacted with the prolyl endopeptidase and prolidase sequentially, then the edible peptide-containing material should be contacted with the prolyl endopeptidase before being contacted with the prolidase. The optimum temperature for contacting the edible peptide-containing material with the prolyl endopeptidase in an aqueous dispersion will depend on exact prolyl endopeptidase selected. In the method of the invention the edible peptide-containing material may be contacted with the prolidase in an aqueous dispersion at a temperature of between 45 and 55° C. The edible peptide-containing material may be contacted with the prolidase in an aqueous dispersion at a pH of between 6.3 and 8.2.

The food preparation may be heated to between 60 and 300° C. during the heat treatment according to the method of the invention. The heat treatment may be selected from the group consisting of pasteurization, sterilization, oven baking, roller drying, and extrusion. The heat treatment may be applied during spray drying.

In a second aspect, the invention provides a hydrolysed preparation obtainable by contacting an edible peptide-containing material with a prolidase, wherein the prolidase comprises an amino acid sequence having at least 95% identity to SEQ ID NO:1. The hydrolysed preparation may be obtainable by contacting an edible peptide-containing material with a prolyl endopeptidase and a prolidase, wherein the prolidase comprises an amino acid sequence having at least 95% identity to SEQ ID NO:1. For example the prolyl endopeptidase may be contacted with the edible peptide-containing material before, or simultaneously with the prolidase. The molar fraction of proline as a free amino acid may be at least a factor of 2 times higher than in a hydrolysed preparation with the same composition except that the edible peptide-containing material has been completely hydrolysed to free amino acids.

The invention may provide a food preparation incorporating a hydrolysed preparation according to the second aspect of the invention. In a further aspect, the invention provides a food preparation comprising a prolyl endopeptidase, a prolidase, proline as free amino acid and ornithine as a free amino acid; wherein the prolidase comprises an amino acid sequence having at least 95% identity to SEQ ID NO:1; and, if leucine is present as a free amino acid, the molar ratio of proline to leucine as free amino acids is greater than 2.5 and the molar ratio of ornithine to leucine as free amino acids is greater than 1. Leucine is responsible for cheesy flavours which are undesirable in many baked goods such as confectionery wafers. The prolyl endopeptidase may for example be a proline-specific endoprotease from *Aspergillus niger*, for example the prolyl endopeptidase may be Maxipro PSP or Maxipro XF from DSM. The invention may provide a heat-treated food product obtainable by heating such a food preparation.

In a still further aspect the invention provides a heat-treated food product obtainable by a method comprising; a) contacting an edible peptide-containing material with a prolidase to form a hydrolysed preparation, wherein the prolidase comprises an amino acid sequence having at least 95% identity to SEQ ID NO:1; b) incorporating the hydrolysed preparation obtainable from step (a) into a food preparation which comprises at least a reducing sugar; or, where the hydrolysed preparation already comprises at least a reducing sugar, the hydrolysed preparation may be the food preparation; and c) subjecting the food preparation to heat treatment to obtain a heat-treated food product. The heat-treated food product may be obtainable by a method comprising; a) contacting an edible peptide-containing material with a prolyl endopeptidase and a prolidase to form a hydrolysed preparation, wherein the prolidase comprises an amino acid sequence having at least 95% identity to SEQ ID NO:1; b) incorporating the hydrolysed preparation obtainable from step (a) into a food preparation which comprises at least a reducing sugar; or, where the hydrolysed preparation already comprises at least a reducing sugar, the hydrolysed preparation may be the food preparation; and c) subjecting the food preparation to heat treatment to obtain a heat-treated food product.

In a still further aspect, the invention provides for the use of a prolidase comprising an amino acid sequence having at least 95% identity to SEQ ID NO:1 to improve the flavour of a heat-treated food product. The prolidase may be used in combination with a prolyl endopeptidase. For example the prolidase may be used after or simultaneously with a prolyl endopeptidase.

Those skilled in the art will understand that they can freely combine all features of the present invention disclosed herein. In particular, features described for the method of the present invention may be combined with the product of the present invention and vice versa. Further, features described for different embodiments of the present invention may be combined. Where known equivalents exist to specific features, such equivalents are incorporated as if specifically referred to in this specification.

Further advantages and features of the present invention are apparent from the figures and non-limiting examples.

EXAMPLES

Example 1: Generation of Amino Acids with Prolyl Endopeptidase and *Klyveromyces lactis* Prolidase Prolidase enzyme from *Klyveromyces lactis* having the SEQ ID NO:1 was expressed (Biocatalysts Ltd. UK). A 10% w/v suspension of wheat gluten was incubated for 10 min at 50° C. and pH 5.5 with $0.4\%_{vs\ prot.}$ prolyl endopeptidase (Maxipro XF from DSM). Then the pH was increased to 7.2, $1.0\%_{prot.\ vs\ prot.}$ of prolidase from *K. lactis* was added and the mixture was again incubated for 24 hours at 50° C. For comparison, wheat gluten was treated under the same pH and incubation conditions but only using the prolyl endopeptidase.

The determination of amino acids was performed using a Nucleodur 100-3 HILIC column. Amino acids were eluted with a gradient of water in acetonitrile, both containing 0.5% acetic acid. The detection is performed using a Triple Quadrupole (QQQ) Mass Spectrometer. Different dilutions of standard solutions were used to determine linear regressions of the ratio between the peak area of each amino acid versus the peak area of the corresponding deuterated amino acid as a function of concentration. The quantities of amino acids obtained are plotted in FIG. 1, the unreacted wheat gluten is also shown (Blank). It can be seen that contacting the wheat gluten with prolyl endopeptidase and the prolidase from *K. lactis* (B) provides a greater yield of proline than using prolyl endopeptidase alone (A).

Example 2: Comparison with Prolyl Endopeptidase/Carboxypeptidase CPD-Y

The combination prolyl endopeptidase/*K. lactis* prolidase was compared with using the combination proposed in WO2005/117595; prolyl endopeptidase/carboxypeptidase CPD-Y. Initially a 49% w/v suspension of wheat flour (corresponding to a 10% w/v suspension of wheat gluten) was incubated for 2 hours at 50° C. and pH 5.0 with $0.4\%_{vs\ prot.}$ prolyl endopeptidase (Maxipro XF) and $0.1\%_{prot.\ vs\ prot.}$ of either the carboxypeptidase CPD-Y (Sigma), or prolidase from *K. lactis* as in Example 1. The activity of carboxypeptidase CPD-Y was found not to be the same as prolidase from *K. lactis* (carboxypeptidase CPD-Y has an overall higher activity) so, to evaluate the selectivity of the enzymes, further experiments were performed with similar extents of conversion, the amount of CPD-Y being reduced compared to the prolidase from *K. lactis*.

Figure 2:
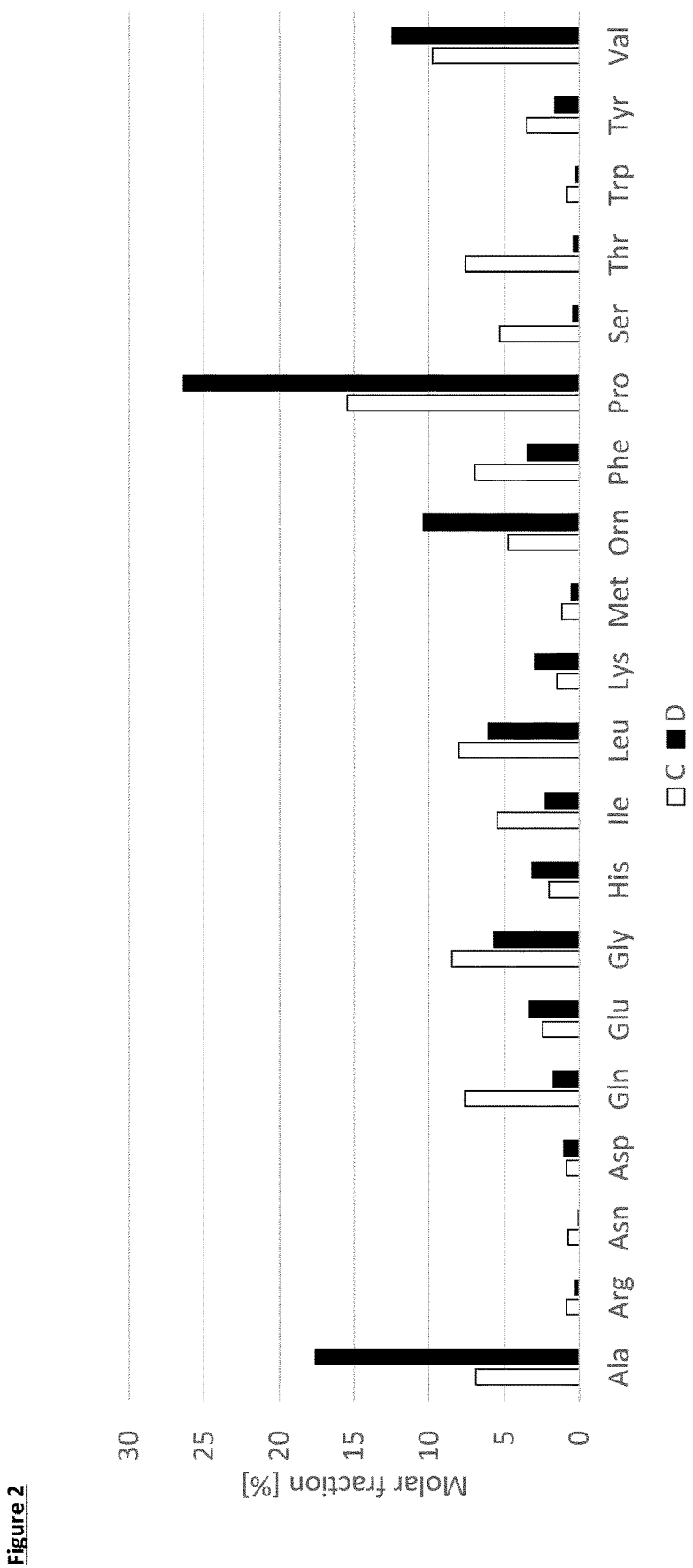
FIG. 2 is a plot of free amino acid molar fractions for wheat gluten incubated with prolyl endopeptidase and CPD-Y prolidase (C) or prolyl endopeptidase and $K.$ $lactis$ prolidase (D).

A 10% w/v suspension of wheat gluten was incubated for 10 min at 50° C. and pH 5.5 with $0.4\%_{vs\ prot.}$ proline specific endopeptidase (Maxipro XF) before being hydrolysed with either $1.0\%_{prot.\ vs\ prot.}$ of prolidase from *K. lactis* or $0.1\%_{prot.\ vs\ prot.}$ of CPD-Y. The pH was increased to 7.2 and the mixture was incubated for about 24 hours at 50° C. The free amino acids produced are shown in FIG. 2. The amounts of amino acids are given as molar fractions. The molar fraction represents the proportion of one individual amino acid versus the sum of all free amino acids present after enzymatic hydrolysis. It is a simple way to illustrate the selectivity of the enzyme. It can be seen that prolidase from *K. lactis* (D) has a much greater specificity for proline and ornithine production than CPD-Y (C). This is beneficial, as both proline and ornithine generate attractive baked flavours in the Maillard reaction. In addition, prolidase from *K. lactis* produced less leucine than CPD-Y. Leucine is responsible for cheesy flavours which are undesirable in many baked goods such as confectionery wafers. The ratio of proline to leucine was 1.9 for CPD-Y, but was 4.3 for the *K. lactis* prolidase. The ratio of ornithine to leucine was 0.6 for CPD-Y, but was 1.7 for the *K. lactis* prolidase.

Example 3: Autolysis of *Klyveromyces lactis*

Casein peptone (CP) medium was prepared by dissolving 10 g of yeast extract, 20 g of casein peptone and 20 g of dextrose per litre of water. The solution had a pH around 6.5 and was further sterilized by filtration through 0.2 μm filter. *Kluyveromyces lactis* yeast (strain CBS141) was cultivated in the CP medium. An inoculum was prepared from glycerol stock of the yeast strain stored at −80° C. A first culture was carried out inoculating 10 mL of fresh CP medium with 2% of the strain stock. Afterwards, a second culture was performed, inoculating 10 mL of fresh CP medium with 2% of the first culture. The broth was then incubated in a shaker for 24 h at 30° C. and 130 rpm, under aerobic conditions. Fermentation was performed in small fermenter containing CP medium under the following conditions; inoculation 1% v/v, temperature 30° C., aerobic condition controlling the dissolved oxygen at a minimum level of 30%. Depletion of sugars in the growth medium reflects the depletion of nutrients in the growth medium and indicates the end of microorganism growth. Sugars were determined by HPLC, combining ion exclusion and partition (column Aminex HPX-87H, 300×7.8 mm). Sugars were eluted with 0.6 mL/min 5 mM sulfuric acid and detected using a refractive index detector. Different dilutions of standard solutions were used to determine linear regressions of peak area as a function of the concentration.

Figure 3:
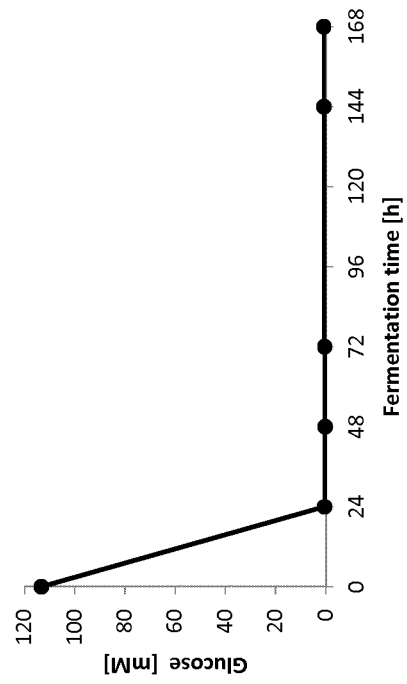
FIG. 3 shows the consumption of glucose (mM) over time (h) during $K.$ $lactis$ fermentation in casein peptone medium as a result of experiments described in Example 3

Maximal growth was obtained within 24 h when glucose was completely depleted, see FIG. 3.

Microorganism cell autolysis is indirectly measured on the basis of enumeration of viable microorganism cells in the growth medium. The method used was to count the number of Colony Forming Units per millilitre (cfu/mL) of fermentation broth. Serial dilutions of the sample were used to find the appropriate concentration where every single viable cell is isolated from the others. Diluent was composed of 1 g tryptone and 8.5 g sodium chloride per litre of water. Aliquots of different dilutions (20 μL) were then deposited onto an YPD (Yeast peptone dextrose) agar plate. After drying, the plates were incubated at 30° C. for 48 h. Each of the previous steps was performed in sterile conditions. Finally, the colonies were counted and viable cells count calculated using the equation:

Viable cells count=$N \times 50 \times D$

Where N is the number of colonies in the selected spot and D is the dilution factor.

Figure 4:
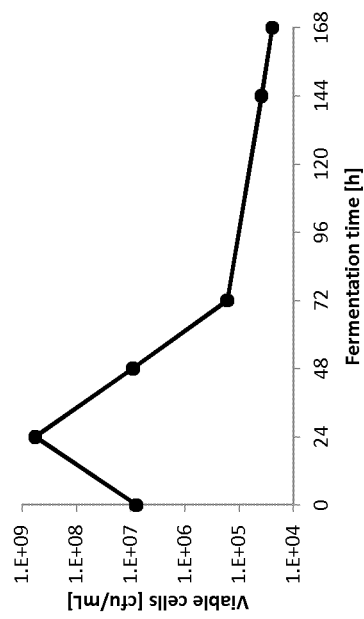
FIG. 4 shows the viability of $K.$ $lactis$ cells (cfu/mL) against fermentation time (h) on casein peptone medium as a result of experiments described in Example 3.

The viability of *K. lactis* cells dropped during prolonged fermentation (see FIG. 4), maintaining the initial conditions in terms of temperature and aerobiosis.

Figure 5:
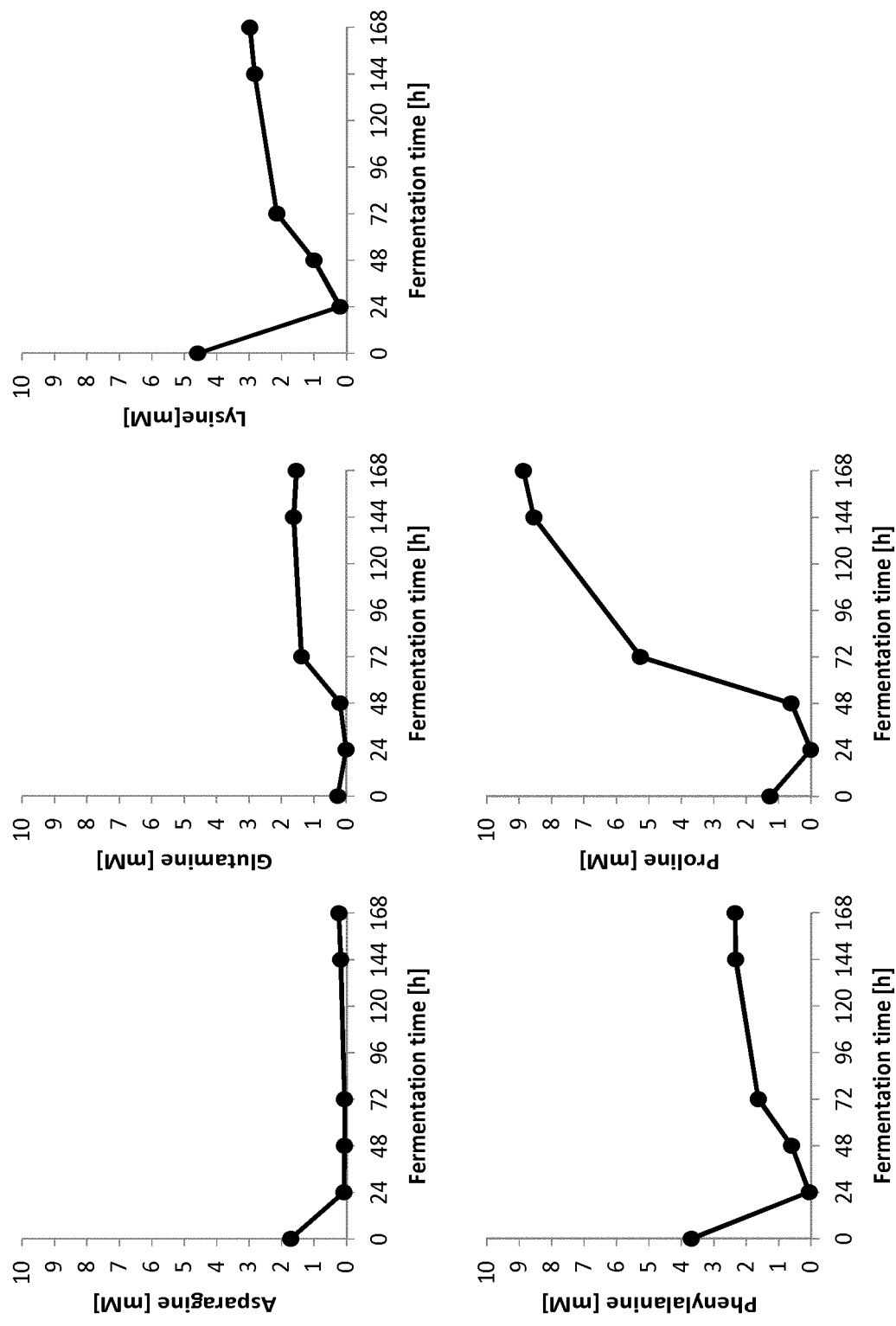
FIG. 5 shows the release of selected free amino acids [mM concentration] during $K.$ $lactis$ fermentation in casein peptone medium as a result of experiments described in Example 3.
Figure 6:
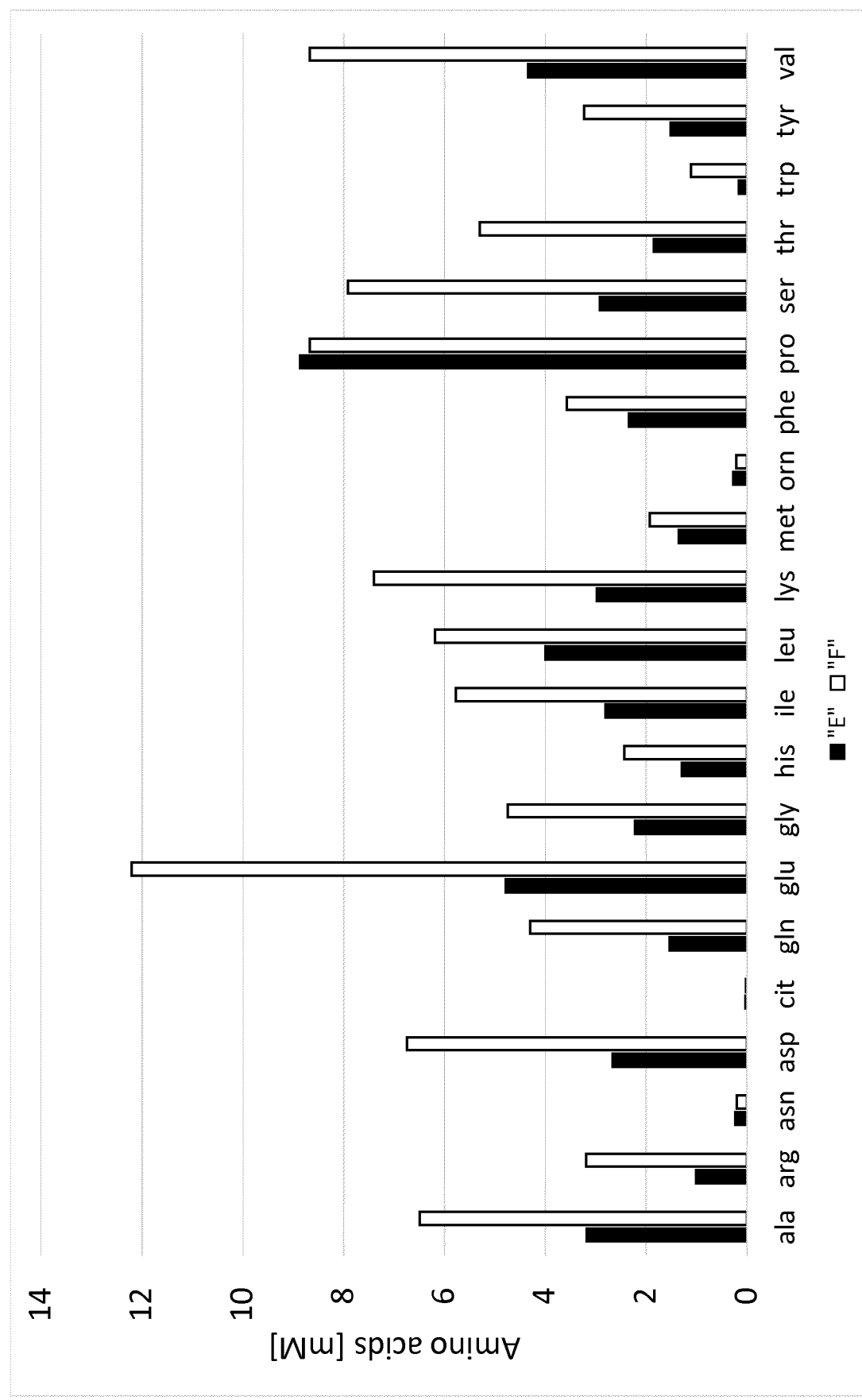
FIG. 6 is a graph showing the free amino acids concentration [mM] obtained 6 days after depletion of glucose as a result of experiments described in Example 3; E (filled bars) is from $K.$ $lactis$ fermentation and F (open bars) is from $S.$ $cerevisiae$. The amino acids are Alanine (ala), Arginine (arg), Asparagine (asn), Aspartic acid (asp), Cittruline (cit), Glutamine (gln), Glutamic acid (glu), Glycine (gly), Histidine (his), Isoleucine (ile), Leucine (leu), Lysine (lys), Methionine (met), Ornithine (orn), Phenylalanine (phe), Proline (pro), Serine (ser), Threonine (thr), Tryptophan (trp), Tyrosine (tyr), Valine (val).

The amount of free amino acids present in the fermentation medium were measured at different times (determination method as in example 1). Results for selected free amino acids are reported in FIG. 5 (time course of amount developed for Asparagine, Glutamine, Lysine, Ornithine, Phenylalanine and Proline). The final measured concentrations [mM] in the fermentation medium for all the released amino acids is reported in FIG. 6—sample E.

Free amino acids that were initially present in CP Medium were totally consumed during the growth of *K. lactis*. Without wishing to be bound by theory, it is believed that as soon as the *K. lactis* cells die, the proteases/peptidases start to hydrolyze the proteins and peptides coming from casein peptone and yeast extract, releasing again free amino acids (see FIGS. 5 and 6), proline being the major one.

It can be seen that *K. lactis*. autolyses and releases prolidase enzymes.

For comparison, the amino acids produced by a temperature sensitive strain of *S. cerevisiae* yeast (CNCM I-4006) were determined (FIG. 6—sample F). *Saccaromyces cerevisiae* CNCM I-4006 was deposited with the Collection Nationale de Cultures de Microorganismes (CNCM), Institut Pasteur, 25 rue du Docteur Roux, F-75724 PARIS Cedex 15, France, on 12 Jun. 2008 and given the deposit number I-4006.

An inoculum was prepared from glycerol stock of the yeast strain stored at −80° C. A first culture was carried out inoculating 10 mL of fresh CP medium with 2% of the strain stock. Afterwards, a second culture was performed, inoculating 10 mL of fresh CP medium with 2% of the first culture. The broth was then incubated in a shaker for 24 h at 25° C. and 130 rpm, under aerobic conditions. Fermentation was performed in small fermenter containing CP medium under the following conditions; inoculation 1% v/v, temperature 25° C., aerobic condition controlling the dissolved oxygen at a minimum level of 30%.

Initial measured pH for the growth medium during cultivation of *S. cerevisiae* yeast (temperature sensitive strain CNCM I-4006) was around 6.5. Maximal growth was obtained within 24 h when glucose was completely depleted.

At 24 h, glucose was added to the medium, up to a concentration of 350 mM within 4 hours. At the same time, temperature was increased from 25 to 37° C.

Glucose was totally consumed during the growth phase and about 250 mM of the added glucose was consumed during the lysis.

It can be seen that *S. cerevisiae* lyses upon application of heat and releases prolidase enzymes. In this experiment, both the *S. cerevisiae* (F) and *K. lactis* (E) yeasts produce similar amounts of proline, however the *K. lactis* strain produces less glutamic acid, leucine and lysine than *S. cerevisiae*. When producing attractive bread-crust and biscuit aromas it is beneficial to limit the quantity of glutamic acid which provides savoury notes, and also leucine and lysine that generate cheesy notes.

Figure 7:
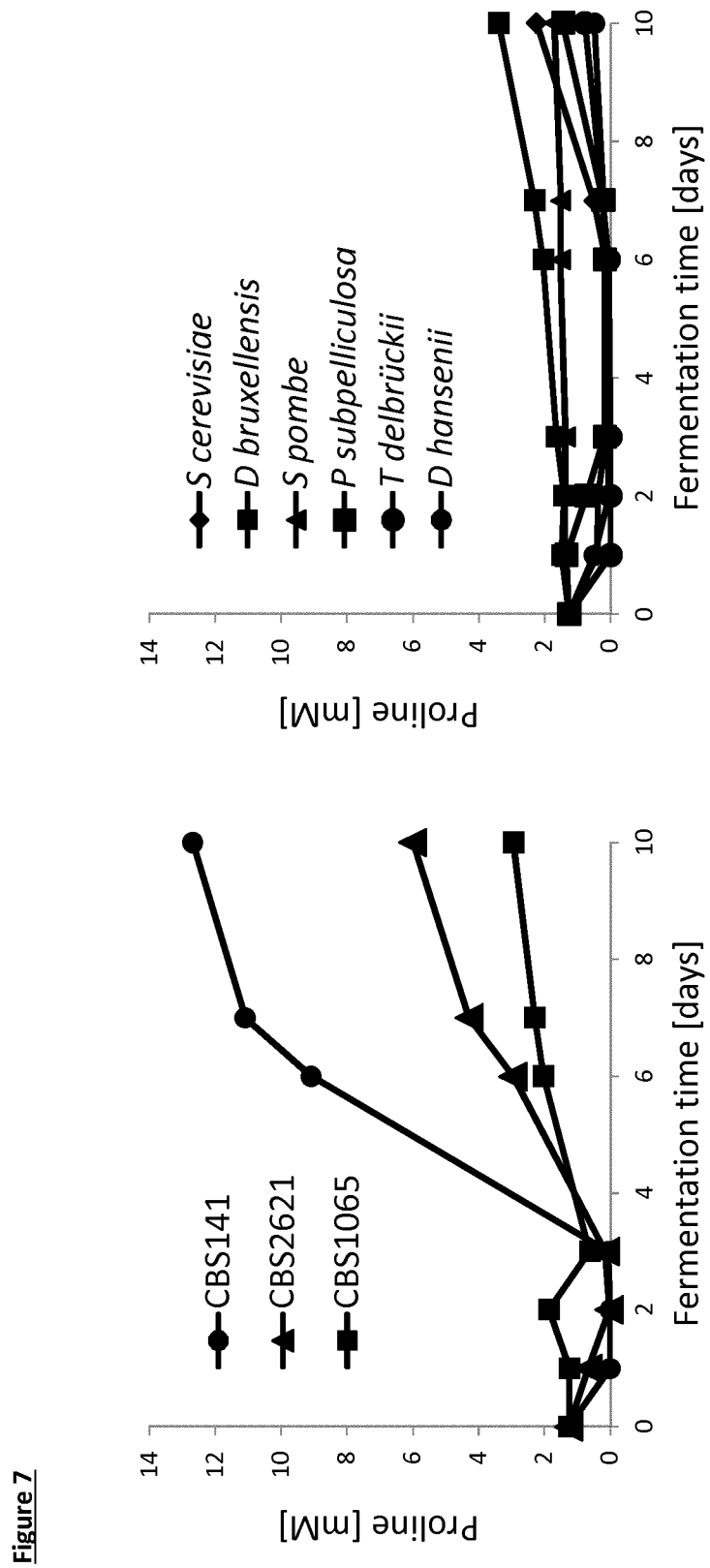
FIG. 7 shows graphs representing the release of proline in prolonged cultivation of $K.$ $lactis$ (different strains) and of other yeast species as a result of experiments described in Example 4.

Example 4: Determination of Proline Released in Fermented Casein Peptone with *K. lactis* when Compared with Other Yeast Species in Prolonged Fermentation Prolonged cultivations of 3 different strains of *K. lactis* (CBS141, CBS2621 and CBS1065) as well as different other yeast species (*Debariomyces hansenii, Dekkera bruxellensis, Pichia subpelliculosa, Saccharomyces Cerevisiae, Schyzosaccharomyces pombe, Torulaspora delbruckii*), were performed, and the amounts of proline in the fermentation medium were measured over the time in the same manner as Example 3 (see FIG. 7). Higher release of proline is achieved in the medium fermented with *K. lactis* than from medium fermented with any other yeast species. Particularly good results were obtained for strains CBS 141 and CBS2621 which died very rapidly in early stationary phase.

Example 5: Preparation of Naked Wafers

Wafer prototypes were prepared to assess the impact of casein peptone fermented with *K. lactis* on the flavour generated during baking. Three variants were compared incorporating, respectively:

Reference

Casein peptone fermented with *K. lactis* (CBS 141) as in Example 3 and freeze dried;

PeptoPro (a commercial milk protein hydrolysate rich in proline, DSM)

Batters having the following formulation were prepared by mixing:

| Ingredient (parts in weight) | Reference | Fermented CP | Peptopro |
| --- | --- | --- | --- |
| Water | 111 | 111 | 111 |
| Flour | 100 | 100 | 100 |
| Salts | 0.41 | 0.41 | 0.41 |
| Fat | 0.59 | 0.59 | 0.59 |
| Rhamnose | — | 0.25 | 0.25 |
| Fermented casein peptone | — | 0.50 | — |
| PeptoPro | — | — | 0.67 |

Wafers were prepared by baking the batter for two minutes in an oven (Haas), between two metal plates heated at 160° C.

The wafers were evaluated by a sensory panel (ten panellists) trained to assess wafers.

Naked wafers were described as follows:

Reference: uncooked, floury

Fermented casein peptone: biscuit, toasted

PeptoPro: floury, wheat

It can be thus concluded that the effect of flavour generated according to the method of the invention is appreciated even in naked wafer, where part of flavour developed on baking is not retained due to the absence of coating.

Example 6: Preparation of Enrobed Wafers

Wafer sheets, prepared according to example 4, were layered with a filling cream and cut to produce a triple-layered wafer biscuit. The layered wafers were then enrobed in chocolate. The same filling and chocolate was used for all samples.

The enrobed wafers were assessed by a sensory panel, trained to assess wafers.

Figure 8:
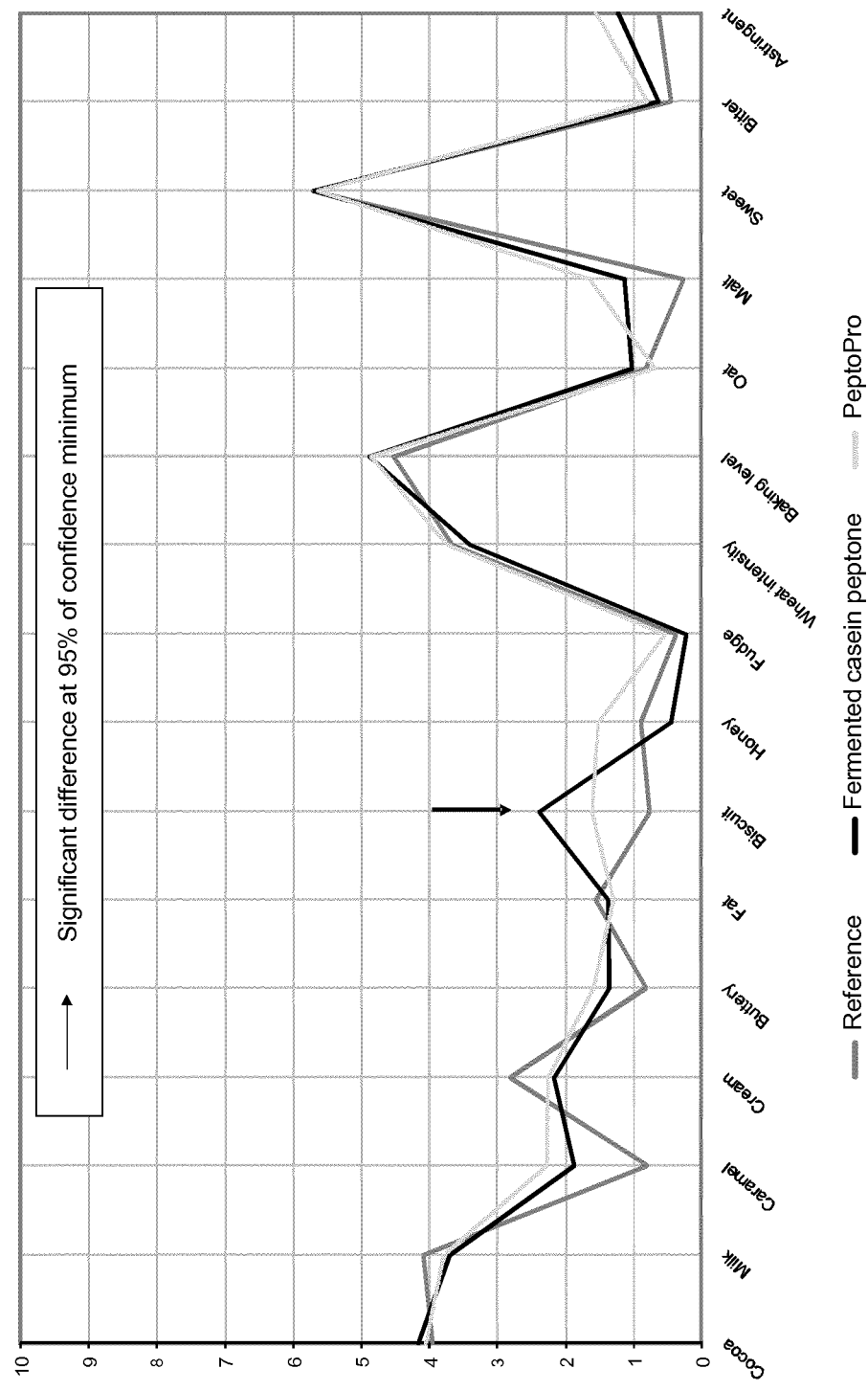
FIG. 8 reports the sensory evaluation profiles for enrobed wafers (Reference—dark grey line; prepared incorporating Fermented Casein Peptone in the batter—black line; and incorporating PeptoPro in the batter—light grey line). Wafers prepared according to experiments described in Example 6. The arrow indicates significant different at 95% confidence minimum for biscuit flavour.

The sensory results are shown in FIG. 8. The enrobed wafers prepared according to the method of the invention show a much stronger biscuit flavour when compared with reference wafers. They also show a stronger biscuit flavour when compared with wafers prepared with a recipe incorporating PeptoPro. The latter, being rich in proline, is expected to deliver a biscuit flavour on baking in the presence of a reducing sugar (rhamnose).

The invention claimed is:

1. A method for flavor generation by release of proline, the method comprising:
   a. contacting an edible peptide-containing material with a prolidase obtained from *Klyveromyces lactis* to form a hydrolysed preparation, wherein the prolidase comprises an amino acid sequence having at least 95% identity to SEQ ID NO:1, and the prolidase is obtained by autolysis of *Klyveromyces lactis*; and
   b. subjecting a food preparation comprising the hydrolysed preparation to heat treatment to obtain a heat-treated food product, wherein the food preparation comprises a reducing sugar that was present in the hydrolysed preparation or added to the hydrolysed preparation, and the heat treated food product is selected from the group consisting of biscuit, extruded cereal, pizza, beverage powder and caramel, wherein the food preparation comprises ornithine as a free amino acid, the food preparation further comprises leucine as a free amino acid, and the molar ratio of the proline to the leucine is greater than 2.5, and the molar ratio of the ornithine to the leucine is greater than 1.

2. The method according to claim 1, wherein the edible peptide-containing material is contacted with a prolyl endopeptidase.

3. The method according to claim 1, wherein the reducing sugar comprises rhamnose.

4. The method according to claim 1, wherein the hydrolysed preparation is incorporated into the food preparation in an amount of 0.01 to 5 parts by weight of the food preparation.

5. The method according to claim 1, wherein the edible peptide-containing material is at least one material selected from the group consisting of flour, milk and peptide-containing components of these.

6. The method according to claim 2, wherein the edible peptide-containing material, the prolyl endopeptidase and the prolidase are contacted in an aqueous dispersion at a temperature of between 30 and 60° C.

* * * * *